United States Patent [19]

Davies

[11] Patent Number: 4,819,632
[45] Date of Patent: * Apr. 11, 1989

[54] RETROLASING CATHETER AND METHOD

[76] Inventor: David H. Davies, 6A Cranmer Road, Cambridge, England, CD3 9BL

[*] Notice: The portion of the term of this patent subsequent to Jun. 16, 2004 has been disclaimed.

[21] Appl. No.: 52,231

[22] Filed: May 19, 1987

Related U.S. Application Data

[63] Continuation of Ser. No. 865,073, May 19, 1986, Pat. No. 4,672,961.

[51] Int. Cl.$^4$ ............................................. A61B 17/36
[52] U.S. Cl. .................................. 128/303.1; 128/398
[58] Field of Search ...................... 128/303.1, 395–398

[56] References Cited

U.S. PATENT DOCUMENTS

| | | | |
|---|---|---|---|
| 1,695,672 | 12/1928 | Wappler | |
| 1,791,794 | 2/1931 | Chesney | 128/398 |
| 3,807,390 | 4/1974 | Ostrowski et al. | 128/2.05 R |
| 3,918,438 | 11/1975 | Hayamizu et al. | 128/4 |
| 4,072,147 | 2/1978 | Hett | 128/303.1 |
| 4,207,874 | 6/1980 | Choy | 128/6 |
| 4,445,892 | 5/1984 | Hussein et al. | 128/303.1 |
| 4,512,762 | 4/1985 | Spears | 128/398 |
| 4,539,987 | 9/1985 | Nath | 128/398 |
| 4,627,436 | 12/1986 | Leckrone | 128/303.1 |
| 4,638,800 | 1/1987 | Michel | 128/303.1 |
| 4,676,231 | 6/1987 | Hisazumi et al. | 128/303.1 X |

*Primary Examiner*—Lee S. Cohen
*Attorney, Agent, or Firm*—Wolf, Greenfield & Sacks

[57] ABSTRACT

An apparatus and method for retrolasing plaque deposits in a coronary artery to remove same includes a tip assembly on the end of a flexible inner tube containing optical fibers that are slidable along a guide wire. The tip assembly includes a reflective surface rearwardly of a front face that directs laser energy supplied through the optical fibers in a rearward direction through a window portion to a focal point externally of the tip assembly. The deposit is removed as the tip assembly is moved in a rearward progression back through the deposit.

16 Claims, 2 Drawing Sheets

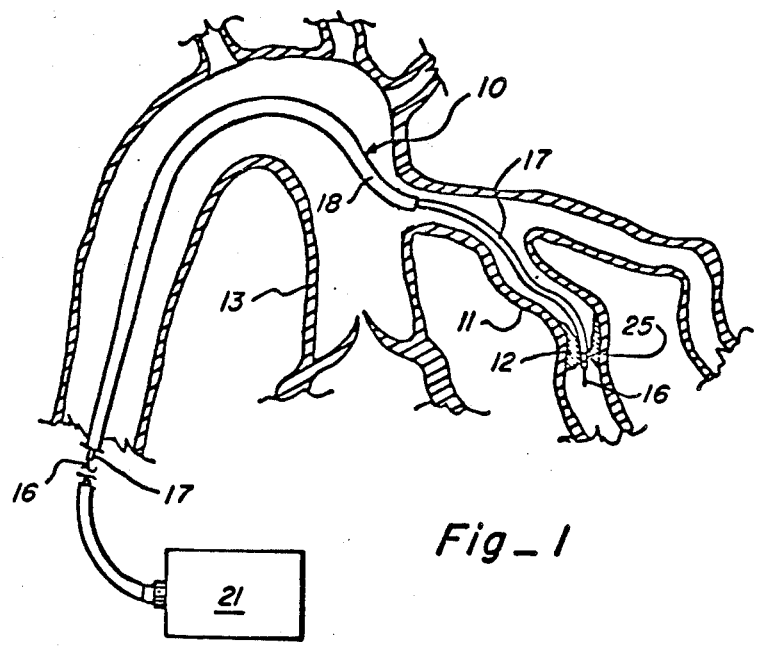
Fig_1
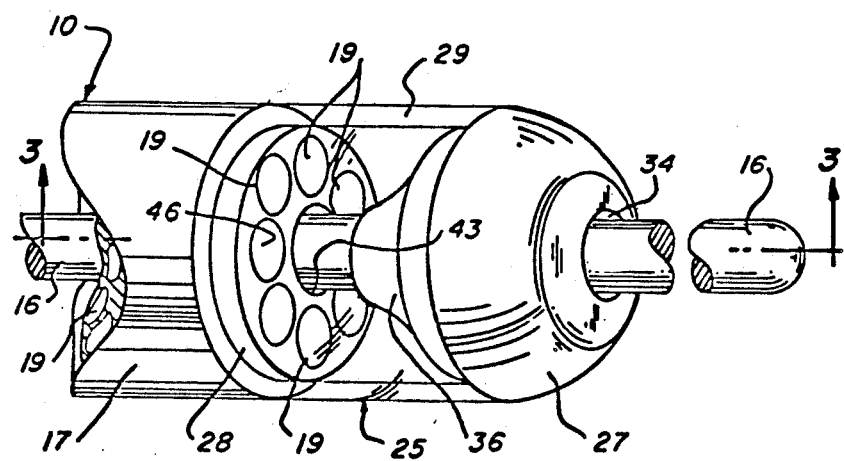
Fig_2

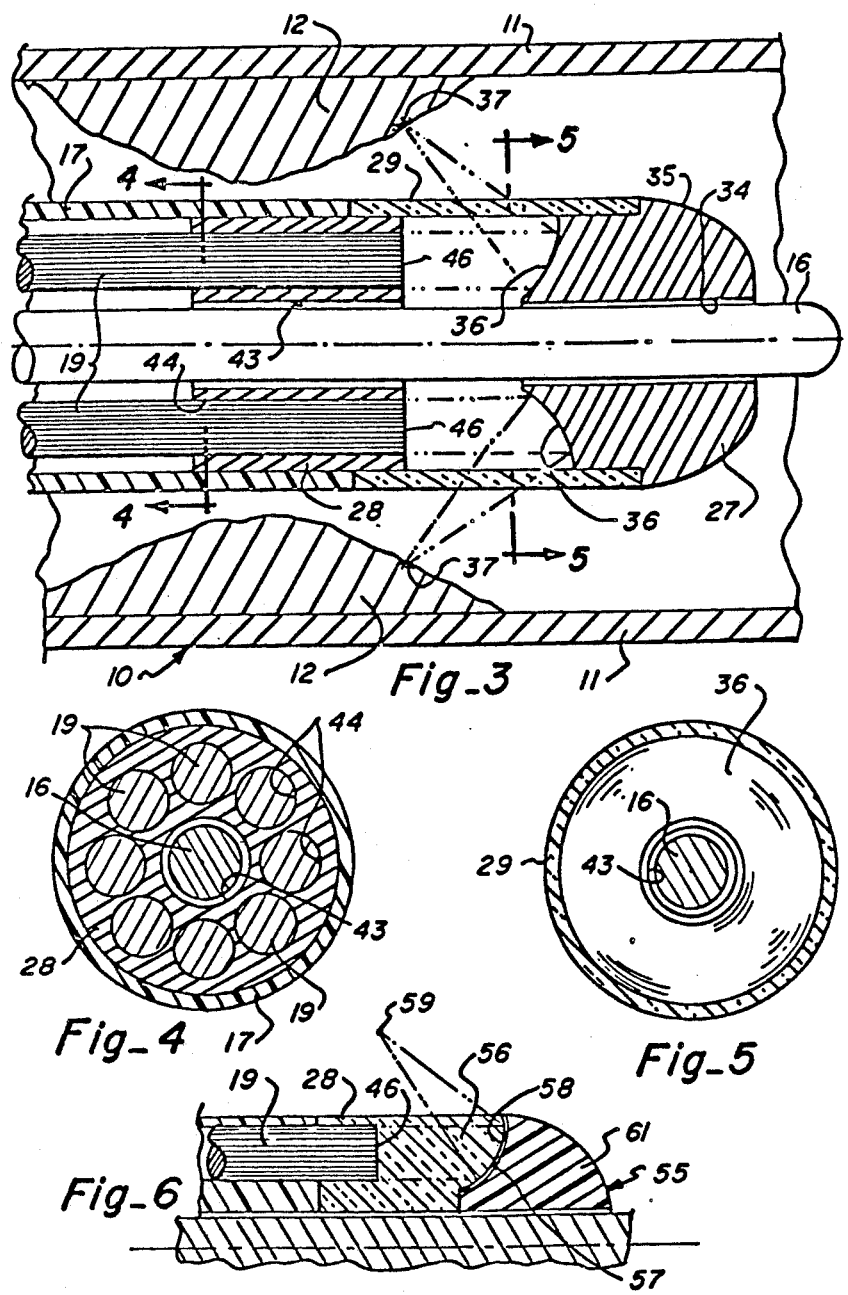

RETROLASING CATHETER AND METHOD

This application is a continuation of application Ser. No. 865,073, filed May 19, 1986, now U.S. Pat. No. 4,672,961.

TECHNICAL FIELD

This invention relates generally to recanalizing blood vessels and more particularly to a novel and improved apparatus and method for removing plaque deposits from diseased arteries.

BACKGROUND ART

Surgical by-pass procedures and balloon angioplasty are two techniques currently available for recanalizing arteries. The techniques of balloon angioplasty involve the passage of a fine guide-wire through the narrowed area, and the advancing of a catheter carrying the balloon through the narrowed area, so that the balloon rests in the narrowed area or site of stenosis. The baloon is then inflated.

In recent years much attention has been given to the use of laser energy for angioplasty. It has been demonstrated that laser energy can be effective in removing atherosclerotic plaque deposits and much research is currently being done to establish effective techniques. Clinical application has been seriously limited, especially in the coronary circulation, by the risk of perforation of the artery. To date the catheter is inserted and the laser energy is directed forward (antegrade lasing) so that in a tortuous artery it is difficult precisely to direct the energy against the deposit. Thus a perforation can be induced, which of course could be lethal.

Representative balloon angioplasty devices and methods using antegrade lasing are disclosed in the U.S. Pat. Nos. 4,207,874, 4,512,762, 4,576,177, and European patent application No. 153,647.

DISCLOSURE OF INVENTION

An apparatus and method for directing laser energy in a coronary artery to remove plaque deposits is disclosed. A tip assembly on the end of a flexible tube containing optical fibers is movable along a guide wire through the artery. The tip assembly has a backwardly facing laser energy reflecting surface, preferably a segment of a parabola, that rearwardly directs and focuses laser energy delivered thereto by the optical fibers on focal points externally to the catheter to remove plaque deposits during a rearward progression of the tip assembly back through the deposit. One form has a front head portion in which the surface is cut and polished. Another form has a reflective coating on the forward curvilinear end of a window body portion that passes laser energy.

BRIEF DESCRIPTION OF THE DRAWINGS

FIG. 1 is a schematic diagram showing a retrolasing catheter in place in a coronary artery.

FIG. 2 is a perspective view of one form of tip assembly of the retrolasing catheter.

FIG. 3 is a sectional view taken along lines 3—3 of FIG. 2.

FIG. 4 is a sectional view taken along lines 4—4 of FIG. 3.

FIG. 5 is a sectional view taken along lines 5—5 of FIG. 3.

FIG. 6 is a fragmentary sectional view showing an alternative form of tip assembly.

DETAILED DESCRIPTION

Referring now to the drawings, there is shown in FIG. 1 a retrolasing catheter 10 embodying features of the present invention in a coronary artery 11. In particular the artery illustrated is the left anterior descending artery which has what is commonly referred to as a plaque deposit 12 which narrows the artery. The catheter 10 is shown as extending through the aorta 13 and into the artery 11 as is conventional practice in balloon angioplasty.

The catheter 10 shown is comprised of an inner guide wire 16 of a length that will extend through the artery and pass through the deposit 12, a flexible inner tube 17 telescoping over and slidable along the guide wire and a flexible guiding tube 18 that telescopes over a portion of inner tube 17 and extends as far as the entrance to artery 11. There is further provided within tube 17 a plurality of circumferentially spaced optical fibers 19 that extend from a source of laser energy 21 located externally of the patient's body to the distal end of the inner tube 17 which conduct laser energy therethrough.

A tip assembly 25 is provided at the distal end of the inner tube 17 which in general includes a front head portion 27, an intermediate tubular portion 29 arranged along a common longitudinal axis and a rear template portion 28.

The front head portion 28 has a central bore 34 through which guide wire 16 extends, a rounded nose or front face 35 to facilitate its being pushed through the artery with a minimum of resistance and a rearwardly diverging rear face 36. The rear face 36 has a curvilinear shape, preferably a segment of a parabola, with a focus or focal point 37 a selected distance beyond the external peripheral surface of the tip assembly. The axis of the parabola is arranged parallel to the longitudinal axis of the tip assembly and the optical fibers are arranged along and parallel to the longitudinal axis of the assembly so that the laser energy passing from the end surface 46 will strike the surface and pass through the focal point of the parabolic surface 36. Since the assembly is tubular in form the parabolic surface extends around the longitudinal axis of the assembly a full 360° to remove the deposits.

The rear face 36 is a mirror or reflective surface that will reflect laser energy. In this form the head portion 27 is preferably made of silver with the rear face machined therein and polished to provide the reflective surface.

The template portion 28 has a central bore 43 extending along the longitudinal axis of the assembly through which the guide wire extends and a plurality of circumferentially spaced positioning bores 44 arranged parallel to the longitudinal axis through which an optical fiber extends. Thus the template portion functions to precisely position the ends of the fibers in relation to the reflective surface. The fiber ends are spaced a selected distance from the longitudinal axis and are equally spaced from one another to provide a balanced array. The distal end 46 of each optical fiber 19 is cut at right angles to the axis of the fiber and each terminates in a common plane along the front face of the template portion and directs laser energy against rearwardly facing reflective face 36 from which it is focused on focal point 37 a selected distance externally of the tip assembly 25. As shown in FIG. 3, the reflective face 36 reflects substantially all of the laser energy delivered through optical fibers 19 in a range of acute angles to the longitudinal axis of the assembly.

The intermediate tubular portion 29 is translucent to laser energy and preferably is made of sapphire to form a window capable of passing laser energy therethrough.

Referring now to FIG. 6, there is shown an alternative tip assembly 55 wherein a tubular body 56 translucent to laser energy, preferably sapphire, is provided. This tubular body forms a window for the laser energy and is solid between the ends 46 of the optical fibers 19 and template portion 28 and a curvilinear front end surface. The front end surface of body 56 is coated with a coating 57 of silver or the like to provide a reflective surface 58 to direct the laser energy to focal points 59 around the external peripheral surface of the tip assembly. In this form, a rounded front nose 61 forwardly of the coating of plastic or the like facilitates movement of the tip assembly 55 through the artery.

A pulsed excimer operating in the ultraviolet range has been found to provide satisfactory results for the source of laser energy 21. For instance, ablation of calcified plaque is probably most efficiently carried out in the ultraviolet range rather than the visible spectrum. A suitable example is light energy having a 308 nm wavelength, 70 ns pulse duration, giving 111 mJ/mm$^2$. The optical fibers appear to sustain this without damage. Pulses having a 40 ns duration have also been found satisfactory.

By way of example and not limitation the following dimensions would be suitable for the above described device:

length of tip assembly 25: 2.5 mm;
diameter of tip assembly 25: 1-1.5 mm;
distance of focal point from surface of tip assembly 25: ½-1 mm;
diameter of guide wire 16: 0.33 mm;
diameter of optical fiber 19: 0.33 mm.

In use, the catheter 10 is inserted into the artery 11 so that the guide wire 16 passes through the deposit 12. The inner catheter tube 17 and tip assembly 25 is slipped over the guide wire and advanced until the tip assembly has passed the deposit 12. The laser energy is transmitted from source 21 through the optical fibers and is reflected back from surface 36 to the focal points 47 of the reflective surface as the tip assembly is retracted to remove the deposit. In this way, the directing of the energy against the deposit can be carefully controlled to avoid perforating the artery.

Although the present invention has been described with a certain degree of particularly, it is understood that the present disclosure has been made by way of example and that changes in details of structure may be made without departing from the spirit thereof.

What is claimed is:

1. A catheter adapted to be inserted in a body passage, comprising:
    a flexible tube having a proximal end and a distal end, having a forward direction from the proximal end toward the distal end and having a reverse direction from the distal end toward the proximal end;
    at least one optical fiber having a distal end and extending through said tube to transmit laser energy in the forward direction from a source to said distal end of said tube; and
    tip assembly means for reflecting substantially all of the laser energy delivered through the distal end of said at least one optical fiber in a range of acute angles to said reverse direction for treatment with the laser energy of a selected portion of said body passage.

2. A catheter as defined in claim 1 wherein said tip assembly means comprises a reflecting surface for reflecting laser energy delivered through said at least one optical fiber and a window portion through which said laser energy is transmitted for treatment.

3. A catheter as defined in claim 2 wherein said reflecting surface is contoured to focus said laser energy external to said catheter.

4. A catheter as defined in claim 1 wherein said tip assembly means includes means for focusing laser energy delivered through said at least one optical fiber on a region external to said catheter.

5. A catheter as defined in claim 1 including a plurality of optical fibers extending through said tube and wherein said tip assembly means includes means for reflecting laser energy delivered through said plurality of optical fibers in a ring-like pattern substantially surrounding said catheter.

6. A catheter as defined in claim 1 wherein said tube is of suitable size and flexibility to be advanced through a blood vessel to a treatment size.

7. A catheter adapted to be inserted in a body passage, comprising:
    a flexible tube having a distal end,
    at least one optical fiber having a distal end and extending through said tube to transmit laser energy from a source to said distal end of said tube; and
    a tip assembly on the distal end of said tube, said assembly having a window portion and a backwardly facing laser energy reflective surface for reflecting substantially all of the laser energy delivered through the distal end of said optical fiber in a reverse direction back through said window portion for treatment of a selected portion of said body passage.

8. A catheter as defined in claim 7 wherein said reflecting surface is contoured to focus said laser energy a selected distance beyond an external surface of said catheter.

9. A catheter as defined in claim 7 including a plurality of optical fibers extending through said tube and wherein said tip assembly includes means for reflecting laser energy delivered through said plurality of optical fibers in a ring-like pattern substantially surrounding said catheter.

10. A catheter as defined in claim 7 wherein said tube is of suitable size and flexibility to be advanced through a blood vessel to a treatment site.

11. A catheter for transluminal angioplasty of a stenosed artery, comprising:
    a catheter lead having a proximal end and a distal end, said catheter lead having a suitable diameter and flexibility to be advanced through the artery to a region that is stenosed by deposits;
    at least one optical fiber extending through said catheter lead to transmit laser energy in a forward direction from a source to said distal end of said catheter lead; and
    a tip assembly attached to the distal end of said catheter lead and including means for reflecting the laser energy delivered through the distal end of said at least one optical fiber in a reverse-directed beam having sufficient energy to remove deposits in said stenosed region.

12. A catheter as defined in claim 11 including a plurality of optical fibers extending through said catheter lead and wherein said tip assembly includes means for reflecting laser energy delivered through said plurality of optical fibers such that said beam has a circumferential pattern substantially surrounding said catheter lead.

13. A catheter as defined in claim 11 wherein said tip assembly includes means for focusing laser energy delivered through said at least one optical fiber on a region external to said catheter lead.

14. A catheter as defined in claim 11 wherein said beam forms an acute angle with the reverse direction along said catheter lead.

15. A method for transluminal angioplasty of a stenosed artery, comprising the steps of:
   directing laser energy through an optical fiber in a forward direction from a source to a region of the artery that is stenosed by deposits; and
   reflecting the laser energy delivered through the optical fiber in a reverse-directed beam having sufficient energy to remove deposits in said stenosed region.

16. A method as defined in claim 15 further including the step of focusing the reverse-directed beam on said deposits.

* * * * *